(12) United States Patent
Kim et al.

(10) Patent No.: US 6,638,968 B1
(45) Date of Patent: Oct. 28, 2003

(54) USE OF PRODIGIOSIN FOR TREATING DIABETES MELLITUS

(75) Inventors: Hwanmook Kim, Taejon (KR); Sangbae Han, Cheongju-si (KR); Changwoo Lee, Taejon (KR); Kihoon Lee, Taejon (KR); Sehyung Park, Taejon (KR); Youngkook Kim, Taejon (KR)

(73) Assignee: Korea Research Institute of Bioscience and Biotechnology, Taejon (KR)

( * ) Notice: Subject to any disclaimer, the term of this patent is extended or adjusted under 35 U.S.C. 154(b) by 0 days.

(21) Appl. No.: 10/149,139

(22) PCT Filed: Aug. 10, 2000

(86) PCT No.: PCT/KR00/00881
§ 371 (c)(1),
(2), (4) Date: Jun. 10, 2002

(87) PCT Pub. No.: WO01/60361
PCT Pub. Date: Aug. 23, 2001

(30) Foreign Application Priority Data

Feb. 15, 2000 (KR) ............................................. 2000/7139

(51) Int. Cl.[7] ................... C07D 207/30; A61K 31/4025
(52) U.S. Cl. ...................................... 514/422; 548/518
(58) Field of Search ........................... 548/518; 514/422

(56) References Cited

U.S. PATENT DOCUMENTS 5,691,334 A * 11/1997 Doria et al. ............. 514/235.5
5,847,127 A * 12/1998 D'Alessio et al. .......... 544/141

FOREIGN PATENT DOCUMENTS

WO    99/15690 A    4/1999

OTHER PUBLICATIONS

Tsuji et al., Selective immunosuppression of prodigiosin 25-C and FK506 in the murine immune system' In: J Antibiot (Tokyo), Oct. 1990 43:10, pp. 1293–1301.

* cited by examiner

Primary Examiner—Joseph K. McKane
Assistant Examiner—Kamal Saeed
(74) Attorney, Agent, or Firm—Birch, Stewart, Kolasch & Birch, LLP

(57) ABSTRACT

The present invention relates to a novel use of prodigiosin for treating diabetes mellitus. The prodigiosin can treat or prevent diabetes mellitus without any side effect.

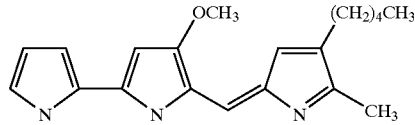

1 Claim, 4 Drawing Sheets

USE OF PRODIGIOSIN FOR TREATING DIABETES MELLITUS

This application is the national phase under 35 U.S.C. §371 of PCT International Application No. PCT/KR00/00881 which has an International filing date of Aug. 10, 2000, which designated the United States of America.

TECHNICAL FIELD

The present invention relates to a novel prodigiosin from *Serratia marcescence* for treating diabetes mellitus.

BACKGROUND ART

Diabetes mellitus and its complications are diseases with a high fatality rate in the world, together with cancer and cardiovascular diseases. According to a report issued by the National Commission on Diabetes, the fatality rate of diabetes is still continuously increasing. Diabetic patients, compared to normal persons, are highly susceptible to suffer from such complications as blindness, kidney disease and heart disease. Now, by the insulin therapy the acute or fatal symptoms of diabetes can be controlled, but the long-term complications reduce life expectancy. Diabetes mellitus is classified into insulin-dependent diabetes mellitus (Type 1) and non-insulin-dependent diabetes mellitus (Type 2). Insulin-dependent diabetes mellitus is caused by damage of insulin-producing pancreatic beta cells, which leads to decrease of the amount of insulin and finally results in hyperglycemia.

Most insulin-dependent diabetes mellitus is the consequence of progressive beta-cell destruction during an asymptomatic period, often extending over many years. In the prediabetic period, circulating islet-cell autoantibodies and insulin autoantibodies may be detected. Insulin-dependent diabetes mellitus has been regarded as an autoimmune disease, and this hypothesis has been strengthened by the studies on the nonobese diabetic (NOD) mice and the BioBreeding (BB) rats. Both of these animals develop insulin-dependent diabetes mellitus spontaneously and their diabetic syndromes share many pathological features with that of humans with insulin-dependent diabetes mellitus. NOD mice, which can naturally fall into insulin-dependent diabetes mellitus, may usually start to expose the symptoms of diabetes in 12~14 weeks, and 80% of all mice have the symptoms. Immunocytes may be activated by unknown factors, and permeate into pancreatic ducts. In the islet, the immunocytes destroy beta cells and then bring about diabetes. Insulin acts on muscle, liver or fat cells to promote glucose metabolism and to lessen the level of glucose in blood. The diminution of insulin in blood by destruction of beta cells leads to deactivation of glucose metabolism in muscle or liver cell, resulting in diabetes mellitus. It has been reported in many studies that beta cell antigen, macrophages, helper T cells, cytotoxic T cells (CTLs), and the like are concerned with the outbreak of diabetes mellitus, and that oxygen free radical or cytokine from immunocytes are responsible for destruction of beta cells.

The genus, Streptomyces or Serratia can produce a red substance of pyrrolylpyromethene skeleton, which is one of following substances: prodigiosin, metacycleprodigiosin, prodigiosen, desmethoxy prodigiosin, and prodigiosin 25-C. These substances have been known to have an antibiotic and anti-malarial effect, especially for prodigiosin 25-C to show immunosuppressing activity. The separation method of prodigiosin has already been reported by the present inventors (KR Application No. 47869, 1997.9.20). Soil sample, which was collected at the beach of Mokpo, Jeollanamdo in Korea, was washed and diluted with DW, and then some microorganism was isolated from the soil sample using the minimal media (Yeast extract 0.1%, polypeptone 0.5%, $K_2HPO_4$ 0.05%, $MgSO_4 7H_2O$ 0.02%, Agar 1.5%, pH 7.2). The minimal media also contained 1 ml of antibiotics (colistin 5 mg/L DW) and 1 ml of nalidixic acid (10 mg/L methanol) in 1 L of media. The isolated strain was denominated as *Serratia marcescence* B-1231 and deposited in Korean Collection for Type Cultures (KCTC 0386BP) on Sep. 19, 1997. To produce immunosuppressive substances, *Serratia marcescence* B-1231 was cultured with 100 ml of the production media (soluble starch 1%, phamamedia 0.5%, glucose 0.2%, ammonium sulfate 0.1%, potassium phosphate 0.1%, magnesium sulfate 0.05%, calcium chloride 0.1%, sodium chloride 0.3%, initial pH 7.0) in 1 L-Erlenmeyer flask at 28° C. for 62 hrs. For extraction of active substance, ethyl acetate equivalent with the culture media was added and the mixture was stirred for 30 minutes, and then the organic phase was decompressed and concentrated to produce an oillike red substance. The crude product was separated and purified using silica column chromatography with chloroform: methanol solution, and further purification was performed using silica-gel thin layer chromatography, resulting in a pure prodigiosin(FIG. 1).

Diabetes research has been directed toward prevention and cure of insulin-dependent diabetes mellitus. Studies on prevention of insulitis and treatment of diabetes has mainly utilized the experimental models of diseases in laboratory animals such as NOD mice, and most therapeutic strategies for treatment of diabetes mellitus are directed to suppression and regulation of autoimmune response in order to prevent beta-cell destruction. Autoimmune disease, insulin-dependent diabetes mellitus results from increasing abnormalities of cellular immunity.

Various immunotherapies for preventing destruction of pancreatic beta-cells have been attempted. Neonatal thymectomy is the method of suppressing the outbreak of diabetes mellitus in NOD mice by killing T lymphocytes. Also, it has been known that depletion of macrophages or T cells using antibodies to T cell-dependent antigens represses diabetes. Some reports discloses that diabetes mellitus can be prevented by controlling production and reaction of free radical, for example, NO released from immunocytes by antioxidants such as nicotinamide, vitamin E, probucol, MDL29311, and U78518F, as has been reported.

To date, researches on immunosuppressive therapy are continued. However, treatment of diabetes mellitus utilizing glucocorticoids and cyclophosphamide has proved to be largely unsuccessful. Although studies on the use of cyclosporin A, rapamycin, and FK506 in diabetes appear to be encouraging, the generalized immunosuppression involves potential complications including infections and drug-induced kidney and liver damage. Recently, many researchers are making efforts to find and develop a therapeutic agent for insulin-dependent diabetes mellitus without any side effect. Although diabetes can be prevented or treated with immunosuppressive agents, these agents can cause some side effects such as immunosuppression and toxicity to liver or kidney.

The present inventors achieved this invention, proving that the prodigiosin from *Serratia marcescence* as a novel immunosuppressive agent prevents and cures autoimmmune diseases with no side effect.

DISCLOSURE OF THE INVENTION

The present invention provides a novel prodigiosin as an active component for preventing and treating diabetes mellitus.

The purpose of this invention was achieved by proving efficiency of the prodigiosin on prevention and cure of diabetes mellitus by administering prodigiosin from *Serratia marcescence* to NOD mice; examining inhibition of cytokine production; and confirming that the diabetes-suppressing effect of the prodigiosin originates from its regulation of immune responses.

The present invention consists of following steps:
the step of comparing the urine glucose level of prodigiosin-injected NOD mice with that of control group, not receiving prodigiosin, in order to verify the diabetes-suppressive effect of prodigiosin from *Serratia marcescence*; the step of observing the transition of pancreatitis to insulitis in prodigiosin-injected NOD mice, comparing to the case of control group, to verify the insulitis-suppressive effect of prodigiosin; the step of measuring the expression level of cytokine mRNA in the separated spleen of NOD mice after a two-day intraperitoneal injection of the inventive prodigiosin, to confirm the diabetes-suppressive activity of the prodigiosin based on its regulation of the cytolcine production; the step of transplanting lienal cells of non-prodigiosin-injected mice to NOD.Scid mice and measuring the occurring level of diabetes, to confirm that the inventive prodigiosin regulates immune responses and suppresses the outbreak of diabetes; and the step of examining their weight and mortality to investigate the side effects of the prodigiosin on NOD mice.

The inventors have examined therapeutic effects of prodigiosin from *Serratia marcescence* on diabetes mellitus. Doses of the inventive prodigiosin were 10 mg/kg/day every other day with intraperitoneal injection. The dose level, route, and schedule of administration, however may vary depending on the condition of the subject.

Prodigiosin suppressed completely crisis of diabetes mellitus of NOD mice. Prevention and cure of diabetes mellitus by the prodigiosin was examined by the test, in which the urine or blood glucose level had been compared to that of control and significant drop was observed. Prodigiosin inhibited lymphocyte infiltration into pancreatic ducts, to suppress insulitis.

Activation of T lymphocytes and macrophages plays an important role in autoimmune disease system. IL-2 and IFN-gamma, which are cytokines from Th1 cells, have significant effects on induction of diabetes mellitus. IL-2 promotes destruction of beta cells by activating cytotoxic T cells (CTLs). IFN-gamma can activate macrophages, and the activated macrophages anplify the antigen presenting function to increase autoimmune responses. Simultaneously, free radicals such as activated oxygen may be increased, resulting in destruction of beta cells. Increase of IL-10 or IL-4 expression by cytokines from Th2 leads to inhibition of function of Th1 cell and consequently decline in autoimmune responses. IL-6 and IL-12 are cytokines expressed by macrophages. Particularly, IL-12, which stimulates Th1 cells to enhance the production of IL-2, performs an important function in inducing autoimmune diseases such as diabetes mellitus. Prodigiosin inhibited expression of such cytokines as IL-2, IFN-gamma, IL-10, IL-6 or IL-12, which play an important part in the occurrence of diabetes mellitus of NOD mice. This regulation of the prodigiosin works as a major factor of suppressing diabetes mellitus.

The inventive prodigiosin was proved to treat diabetes mellitus without any side effect. Because of diabetes, NOD mice have their weight decrease and come to die in 2 weeks after symptoms of diabetes. NOD mice, receiving prodigiosin, have their weight not decrease and any mice were not found dead. This result addresses that the prodigiosin removed diabetes and prevented the death of the mice, as well as has no side effect in animal treatment. Prodigiosin has no toxicity to kidney, liver and lung.

NOD mice are the best disease animal models in studies on insulin-dependent diabetes. NOD mice can naturally fall into insulin-dependent diabetes mellitus and the symptoms are very similar with those of human. The effects of prodigiosin on preventing and treating of diabetes were examined using the NOD mouse model and following examples is presenting more detailed description.

EXAMPLES

The following examples are offered to illustrate this invention and are not meant to be construed in any way as limiting the scope of this invention.

Example 1

Prevention and Cure of Clinical Diabetes by Administration of Prodigiosin

Figure 1:
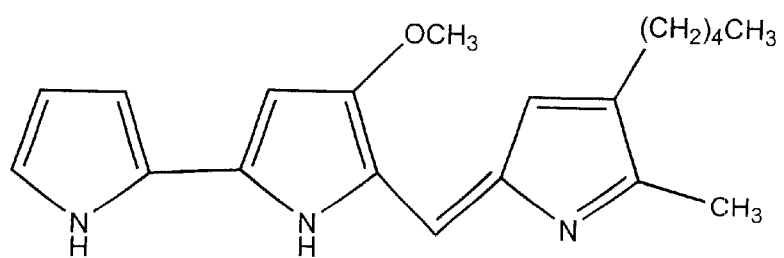
FIG. 1 illustrates the structure of the prodigiosin.
Figure 2:
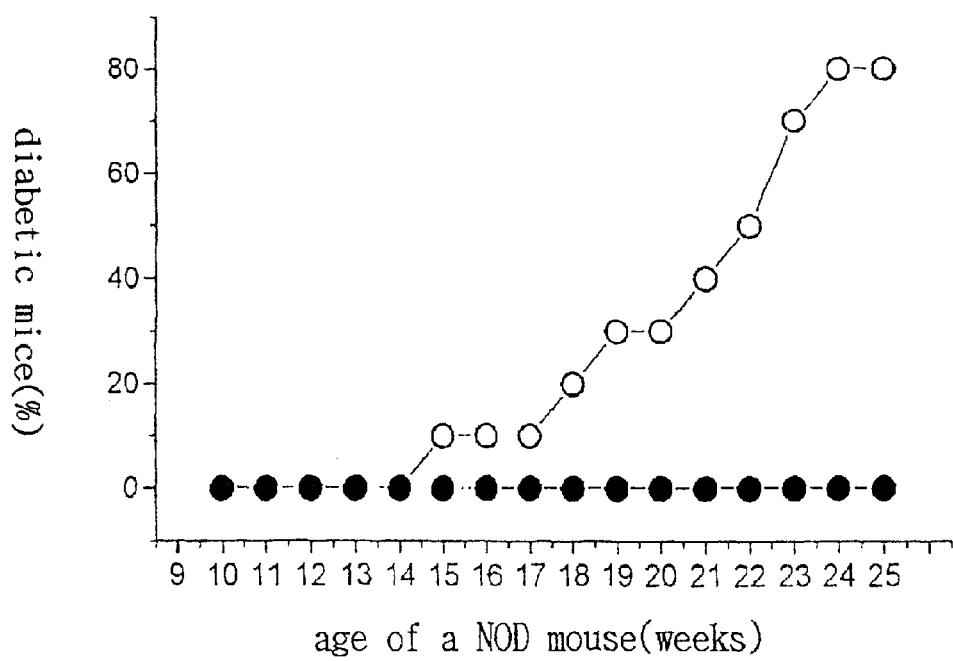
FIG. 2 illustrates prevention and cure of diabetes mellitus by administration of prodigiosin Diabetic mice were selected according to the urine glucose level, and the percentage is based on the total mice (10 heads). Open circles (○) are of control NOD mice and closed circles (●) are of NOD mice receiving prodigiosin.
Figure 3:
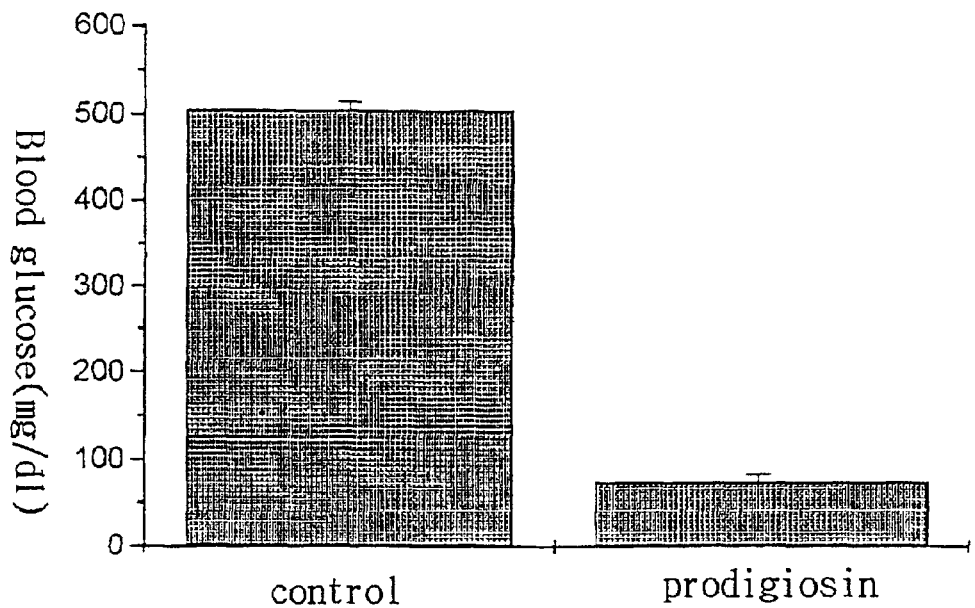
FIG. 3 illustrates decrease of the blood glucose by administration of prodigiosin. After we isolated plasma from NOD mouse, the blood glucose was measured with the blood biochemical analyzer (Cibacorning, USA).

Prodigiosin was intraperitoneally injected in 10 mg/kg from 8 weeks to 24 weeks of age, and the urine glucose was measured with uropaper (Eiken Chemical Co. Ltd., Japan) every week. In control group of NOD mice, not receiving prodigiosin, the urine glucose was first detected from 15 weeks of age, and at 24 weeks, 80% of the mice had the urine glucose detected (FIG. 2). Experimental group of NOD mice with administration of prodigiosin had the urine glucose not detected, and these results show complete suppression of clinical diabetes by administration of prodigiosin. Average blood glucose of non-prodigiosin-injected NOD mice was 500 mg/dl, which means diabetes mellitus crisis, and that of prodigiosin-injected NOD mice was 100 mg/dl, which means the normal condition (FIG. 3). Consequently, it was proved that the prodigiosin could prevent clinical diabetes in NOD mice completely.

Example 2
Suppression of Insulitis by Administration of Prodigiosin

Figure 4:
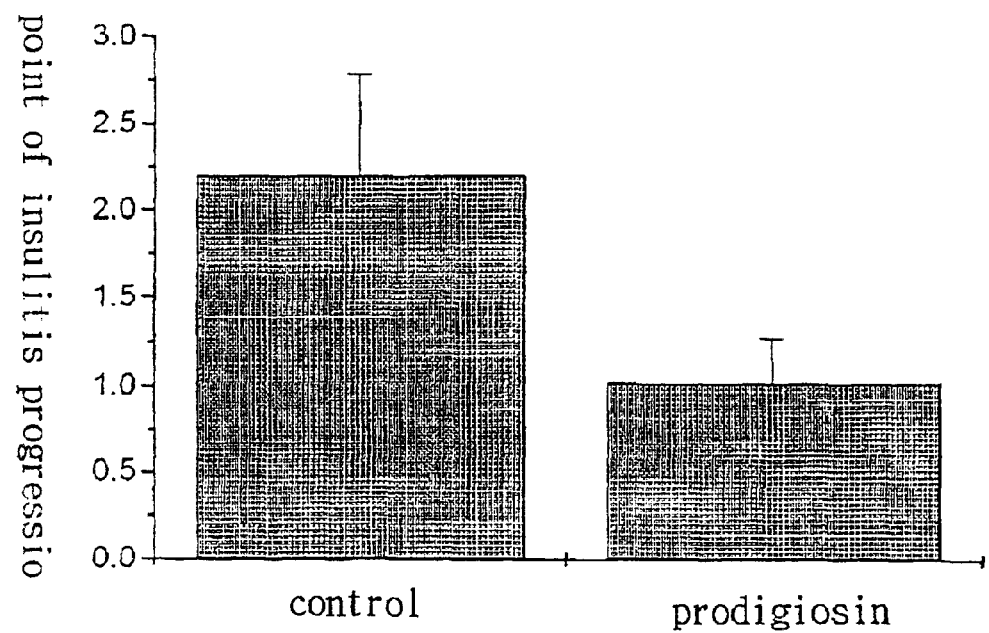
FIG. 4 illustrates decline of insulitis by administration of prodigiosin.
Figure 5:
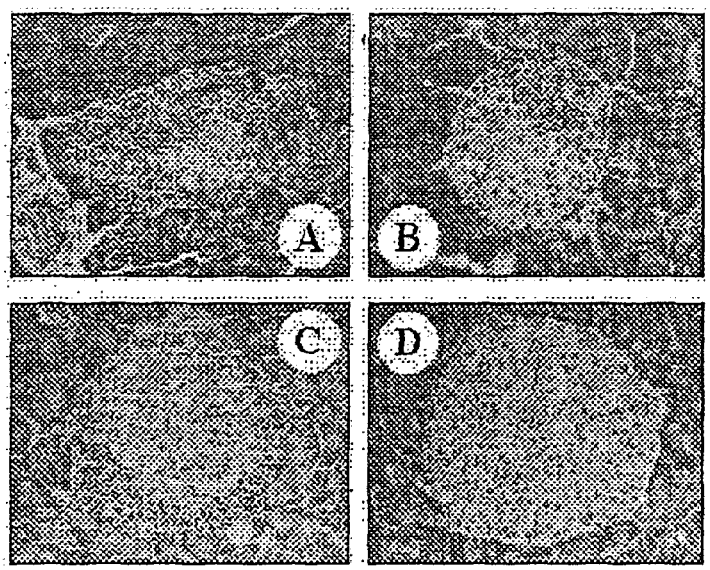
FIG. 5 illustrates decline of insulitis by administration of prodigiosin. Control NOD mice (A) suffered from severe insulitis, but NOD mice receiving prodigiosin (B, C, D) had their insulitis decreased.

In insulin-dependent diabetes mellitus, insulitis may be induced by lymphocyte infiltration into pancreatic ducts and destruction of beta cells thereby. Macrophages and T cells are the major infiltrating lymphocytes, and these immune cells destroy beta cells. The pancreas from both the prodigiosin-injected and the non-injected NOD mice were preserved in formalin and to preparation. After the hematoxylin/eosin staining, the lymphocyte infiltration level was measured. 1, 2, and 3 point were respectively given to 25, 50, and 75% of insulitis progression, and the average value of insulitis progression was calculated (FIG. 4). The NOD mice, not receiving prodigiosin, had more than 2 point, or over 50% of infiltration, while the infiltration level of the prodigiosin-injected mice was about 1 point, or under 20% of infiltration. This result showed that the prodigiosin could suppress the lymphocyte infiltration into pancreatic ducts to debilitate insulitis. FIG. 5 shows the result of pathological tests: A indicates the condition of insulitis of non-prodigiosin-injected mice, showing that most of pancreatic ducts were infiltrated by lymphocytes; B, C, and D show that lymphocyte infiltration was reduced by administration of prodigiosin. This experiment demonstrated that the prodigiosin suppresses insulitis, resulting in prevention of occurrence of diabetes mellitus.

Example 3
Inhibition of Cytokine Production by Prodigiosin

Figure 6:
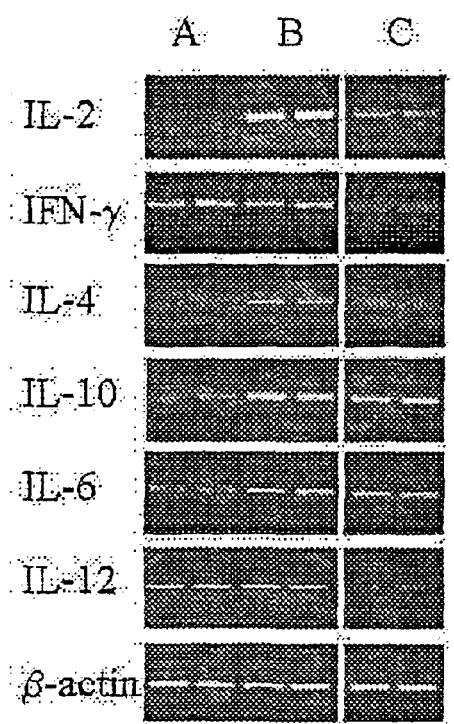
FIG. 6 shows change of expression pattern of lymphocyte's cytokines by administration of prodigiosin. A is of 6-week-old NOD mouse without diabetes, B is of 11-week-old NOD mouse with diabetes, and C is of 11-week-old NOD mouse receiving prodigiosin.

Th cells and macrophages have been known to play an important role in the pathogenesis of diabetes mellitus. According to unknown mechanism, macrophages are activated, and the activated cells produce IL-12. Then IL-12 activates Th1 cells to promote generation of IL-2 and IFN-gamma, and these cytokines activate CTLs and macrophages. The activated CTLs and macrophages destroy beta cells and reduce production of insulin, resulting in occurrence of diabetes mellitus. In this manner, beta cells are disrupted through multi-steps of various mechanisms. Cytokines have a significant part in these immune responses, and control of cytokine production is expected to be prevention and cure of diabetes mellitus. FIG. 6 illustrates the change of cytokine expression of lymphocytes by the prodigiosin. Prodigiosin was intraperitoneally administered to NOD mice from 8 weeks age every other day. In lienal cells from 11-week-old mice, the cytokine MRNA expression level was measured using RT-PCR (the reverse transcription polymerase chain reaction). A is of 6-week-old mouse, B is of 11-week-old one, and C denotes the cytokine expression of 11-week-old mouse receiving prodigiosin. 6-week-old one is of normal condition without the symptoms of diabetes or insulitis, and 11-week-old one is of starting point of insulitis. In other words, the 11-week-old mouse is in the situation that the immunologic functions are abnormally activated and the infiltration is started. At the age of 11 weeks when the functions are brisk, the immunologic functions of mouse's lien cells and their regulation by the prodigiosin were measured. In 11-week-old mouse, mRNA expression of IL-2, IL-10, and IL-6 increased intensively, and by administration of prodigiosin, the expression of IL-2, IFN-gamma, IL-10, IL-6, and IL-12 was strongly suppressed. As you see, the drop of cytokine production results in suppression of its autoimmune responses to beta cells, to cure diabetes meffitus. IL-4 and IL-10 expressed by Th2 cells can weaken the cell function of Th1 cells. The increased expression of IL-4 by the prodigiosin was assumed to inhibit Th1 cell function relating to occurrence of diabetes mellitus. However, the reason of the difference between the expression of IL-10 and that of IL-4 has not been proved. From above results, it becomes clear that the prodigiosin regulates the cytokine production of lymphocytes, resulting in suppressing the occurrence of diabetes mellitus.

Example 4
Side Effects of the Prodigiosin

Figure 7:
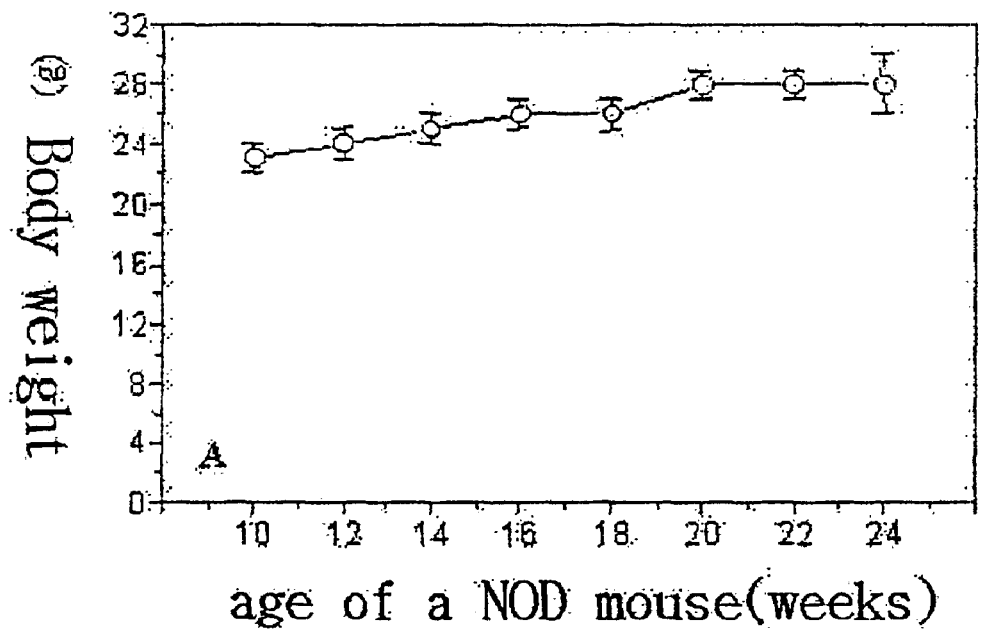
FIG. 7 illustrates that the prodigiosin has no side effect. NOD mice receiving prodigiosir showed no drop of their weight (A), not suffer from toxicity to kidney (B), and anyone was not led to death.
Figure 7:

In NOD mice receiving prodigiosin from 8 weeks to 24 weeks age, the negative effects of the prodigiosin were examined (FIG. 7). After administration of prodigiosin, their body weight didn't decrease and this result means that the prodigiosin has no side effect (FIG. 7A). After their liver, kidney, and lung had been extracted from the prodigiosin-injected NOD mice, a pathological test was performed using the hematoxylinleosin staining. Since the glomerulus and nephric tubule were of normal condition as shown in FIG. 7B, the prodigiosin was proved to have no toxicity to kidney.

By the above examples, it has been verified that prodigiosin of the present invention is an preventing and curing agent for diabetes mellitus to prevent destruction of beta cells by suppressing autoimmune responses.

INDUSTRIAL APPLICABILITY

Through the aforementioned examples, it has been illustrated that prodigiosin from *Serratia marcescence* is a therapeutic agent for prevention and cure of diabetes mellitus without any side effect. Therefore, the present invention is greatly usefull for the medical and pharmaceutical industries relating to prevention and cure of diabetes mellitus.

What is claimed is:

1. A method of treating diabetes mellitus, said method comprising administering a therapeutically effective amount of the following compound,

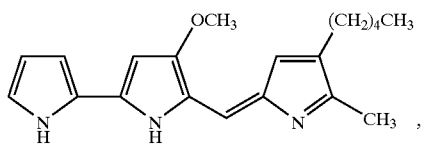

to a patient in need thereof.

* * * * *